(12) United States Patent
Wakamoto et al.

(10) Patent No.: US 10,379,052 B2
(45) Date of Patent: Aug. 13, 2019

(54) TRANSCRIPTOME ESTIMATION DEVICE AND TRANSCRIPTOME ESTIMATION METHOD

(71) Applicant: THE UNIVERSITY OF TOKYO, Tokyo (JP)

(72) Inventors: Yuichi Wakamoto, Tokyo (JP); Koseki Kobayashi, Tokyo (JP)

(73) Assignee: THE UNIVERSITY OF TOKYO, Tokyo (JP)

( * ) Notice: Subject to any disclaimer, the term of this patent is extended or adjusted under 35 U.S.C. 154(b) by 0 days.

(21) Appl. No.: 16/210,311

(22) Filed: Dec. 5, 2018

(65) Prior Publication Data

US 2019/0170649 A1    Jun. 6, 2019

(30) Foreign Application Priority Data

Dec. 6, 2017   (JP) .................................. 2017-234164

(51) Int. Cl.
| | | |
|---|---|---|
| *G01J 3/44* | (2006.01) | |
| *G01N 21/65* | (2006.01) | |
| *C12Q 1/6816* | (2018.01) | |
| *G01L 1/24* | (2006.01) | |
| *G01N 21/01* | (2006.01) | |

(52) U.S. Cl.
CPC ........... *G01N 21/65* (2013.01); *C12Q 1/6816* (2013.01); *G01J 3/44* (2013.01); *G01L 1/242* (2013.01); *G01N 2021/0143* (2013.01); *G01N 2201/067* (2013.01)

(58) Field of Classification Search
CPC ........... G01J 3/44; G01N 21/03; G01N 21/65; G01N 21/64; G01N 33/53; G01N 33/547; G01N 33/566; G01L 1/24; C12Q 1/6816; C01N 33/543; C12N 15/10
See application file for complete search history.

(56) References Cited

U.S. PATENT DOCUMENTS

2015/0276608 A1* 10/2015 Nakashima ........ G01N 33/5011
435/6.18

FOREIGN PATENT DOCUMENTS

JP      2006-236011 A     9/2006
JP      2012-039994 A     3/2012

* cited by examiner

*Primary Examiner* — Abdullahi Nur
(74) *Attorney, Agent, or Firm* — Oliff PLC

(57) ABSTRACT

An objective cell is irradiated with laser beam of a predetermined wavelength. Only Stokes light is selected out of detected light including reflected light and scattered light of the laser beam, and a Raman scattering spectrum is obtained by dispersion of the selected Stokes light. A transcriptome of the objective cells is estimated, based on the Raman scattering spectrum. It is preferable to estimate the transcriptome of the objective cells, based on N-dimensional Raman data obtained by dimensional reduction of the Raman scattering spectrum. This configuration only needs to irradiate the objective cell with the laser beam and does not require to destroy the objective cell. As a result, this enables the transcriptome of the cell to be estimated in a short time period without destroying the cell.

5 Claims, 5 Drawing Sheets

PRESS value of Function A' of
Appropriate Combination ≈ 5.77

TRANSCRIPTOME ESTIMATION DEVICE AND TRANSCRIPTOME ESTIMATION METHOD

CROSS-REFERENCE TO RELATED APPLICATIONS

The present disclosure claims priority to Japanese Patent Application No. 2017-234164 filed Dec. 6, 2017, which is incorporated herein by reference in its entirety including specification, drawings and claims.

TECHNICAL FIELD

The present disclosure relates to a transcriptome estimation device and a transcriptome estimation method.

BACKGROUND

A proposed technique as a method of analyzing a transcriptome calculates a principal component from a data matrix of a change in expression level of the transcriptome, scales the principal component by dividing the principal component by a square root of the number of samples in the data matrix used for the calculation of the principal component or by a square root of the number of measurement items in the data matrix used for the calculation of the principal component, and specifies and selects a change in expression level at a predetermined threshold value from the scaled principal component (as described in, for example, JP 2012-039994A). This method is adaptable to data having different measurement items and having a large number of measurement items, such as transcriptome.

Another proposed technique uses a thermodynamic model to approximate a transcriptome formation mechanism and perform information processing of the transcriptome (as described in, for example, JP 2006-236011A). The thermodynamic model defines the concentration of each mRNA by using an energy parameter of determining a synthesis rate of each mRNA and an energy parameter of determining a degradation rate of each mRNA, and defines the energy parameter by using an intracellular local concentration of a factor having a base sequence-specific binding to RNA or DNA and a characteristic coefficient of a base sequence that is a possible target of the factor. At least one or more of the concentration of mRNA, the intracellular local concentration of the factor, and the characteristic coefficient of the base sequence are entered into the thermodynamic model, and the remaining values are calculated and outputted as unknowns. This linearly analyzes or estimates formation of the transcriptome.

SUMMARY

There is, however, a need to destroy the cell, in order to compute the transcriptome of the cell. It also takes a long time to compute the transcriptome of the cell. There is accordingly a need to compute the transcriptome of the cell in a short time period without destroying the cell.

An object of the present disclosure is to provide a transcriptome estimation device configured to estimate a transcriptome of a cell in a short time period without destroying the cell. Another object of the present disclosure is to provide a transcriptome estimation method of estimating a transcriptome of a cell in a short time period without destroying the cell.

In order to achieve the above primary object, the transcriptome estimation device and the transcriptome estimation method of the present disclosure employs the following configuration.

The present disclosure is directed to a transcriptome estimation device configured to estimate a transcriptome of an objective cell. The transcriptome estimation device includes a laser irradiator configured to irradiate the objective cell with laser beam of a predetermined wavelength, a light selector configured to select only Stokes light out of detected light including reflected light and scattered light by irradiation of the laser beam, a spectroscope configured to disperse the selected Stokes light and output a Raman scattering spectrum, and an estimator configured to estimate the transcriptome of the objective cell, based on the Raman scattering spectrum.

The transcriptome estimation device of this aspect irradiates the objective cell with the laser beam of the predetermined wavelength, selects only the Stokes light out of the detected light including the reflected light and the scattered light of the laser beam and disperses the Stokes light to obtain the Raman scattering spectrum. The transcriptome estimation device of this aspect then estimates the transcriptome of the objective cell, based on the Raman scattering spectrum. This configuration only needs to irradiate the objective cell with the laser beam and does not require to destroy the objective cell. As a result, this enables the transcriptome of the cell to be estimated in a short time period without destroying the cell.

In the transcriptome estimation device of this aspect, the estimator may perform dimensional reduction of the Raman scattering spectrum to N-dimensional Raman data, and may estimate the transcriptome of the objective cell, based on the N-dimensional Raman data. This configuration shortens the time period required for the estimation. In this case, the estimator may apply a conversion function that is based on a linear regression relationship between the N-dimensional Raman data of cells in M different conditions and transcriptomes of the cells in the M different conditions, to estimate the transcriptome. Further in this case, the conversion function may be determined as an inverse function of a function, which is determined by linear regression of the N-dimensional Raman data of the cells in the M different conditions from the transcriptomes of the cells in the M different conditions.

The present disclosure is also directed to a transcriptome estimation method that estimates a transcriptome of an objective cell from a Raman scattering spectrum that is obtained by irradiation of the objective cell with laser beam of a predetermined wavelength. The transcriptome estimation method includes obtaining N-dimensional Raman data by dimensional reduction of Raman scattering spectra of cells in M different conditions, and estimating a conversion function on assumption of a linear regression relationship between transcriptomes of the cells in the M different conditions and N-dimensional Raman data of the cells in the M different conditions, and estimating the transcriptome by applying the conversion function to N-dimensional Raman data obtained by dimensional reduction of a Raman scattering spectrum of the objective cell.

The transcriptome estimation method of this aspect estimates the transcriptome of the objective cell from the Raman scattering spectrum that is obtained by irradiating the objective cell with the laser beam of the predetermined wavelength. The transcriptome estimation method first obtains the N-dimensional Raman data by dimensional reduction of the Raman scattering spectra of the cells in the M different conditions, and estimates the conversion function on the assumption of the linear regression relationship between the transcriptomes of the cells in the M different conditions and the N-dimensional Raman data of the cells in the M different conditions. The transcriptome estimation method then estimates the transcriptome by applying the estimated conversion function to the N-dimensional Raman data obtained by dimensional reduction of the Raman scattering spectrum of the objective cell. This configuration enables the transcriptome of the cell to be estimated in a short time period without destroying the cell.

DESCRIPTION OF EMBODIMENTS

The following describes some aspects of the disclosure with reference to embodiments.

Figure 1:
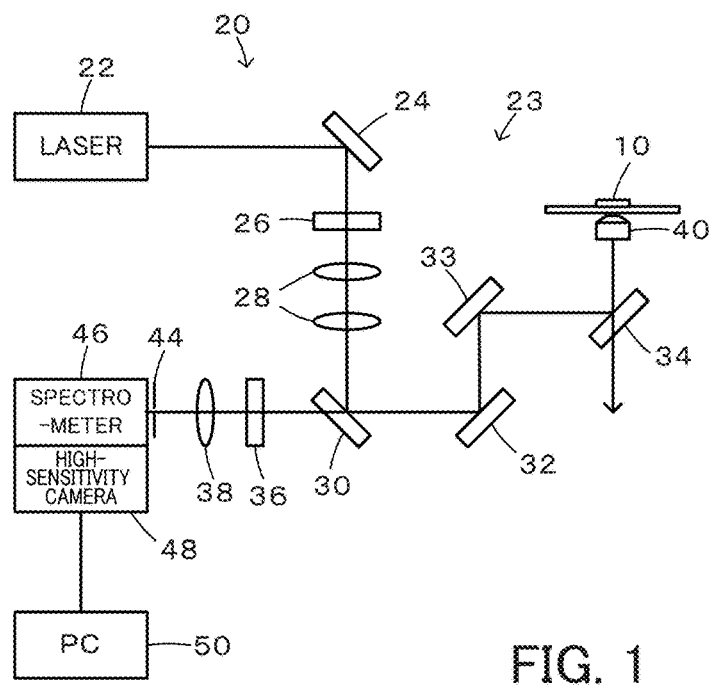
FIG. 1 is a configuration diagram illustrating the schematic configuration of a transcriptome estimation device according to one embodiment of the present disclosure.

FIG. 1 is a configuration diagram illustrating the schematic configuration of a transcriptome estimation device 20 according to an embodiment of the present disclosure. As illustrated, the transcriptome estimation device 20 of the embodiment includes a laser 22 configured to emit laser beam of a predetermined frequency; an optical system 23 configured to guide radiated light from the laser 22 and detected light; an object lens 40 configured to irradiate objective cells 10 as an object of measurement with light radiated from the optical system 23 and to cause detected light (Rayleigh scattered light and Stokes light) to enter therein; a confocal pinhole 44 configured to enhance the spatial resolution of the Stokes light from the optical system 23; a spectrometer 46 configured to cause the Stokes light from the confocal pinhole 44 to enter therein and to be dispersed; a high-sensitivity camera 48 configured to obtain Raman scattering spectra by exposure to the Stokes light dispersed by the spectrometer 46; and a computer (PC) 50 configured by a general-purpose microcomputer to analyze the Raman scattering spectra obtained by the high-sensitivity camera 48.

According to the embodiment, the laser 22 is configured as a semiconductor laser pumped solid-state laser that allows for continuous oscillation of laser beam of wavelength 532 nm. For example, Gem 532 manufactured by Laser Quantum may be used for the laser 22.

The optical system 23 includes a mirror 24; a bandpass filter 26 configured to allow only the laser beam of wavelength 532 nm out of laser beams to pass through; a beam expander 28 configured to expand the beam diameter of the laser beam and thereby adjust a spot size on a measurement object (objective cells 10); a dichroic mirror 30 configured to reflect the laser beam of wavelength 532 nm and the Rayleigh scattered light but to transmit the Stokes light of wavelength equal to or higher than 532 nm; mirrors 32 and 33 configured to guide the laser beam reflected by the dichroic mirror 30; a 90/10 mirror 34 configured to reflect 90% of incident light and transmit 10% of the incident light, with a view to checking a laser spot by a field image; an edge filter 36 configured to transmit only the Stokes light with cutting the Rayleigh scattered light which the dichroic mirror 30 fails to cut; and a lens 38.

According to the embodiment, the spectrometer 46 is configured as a Czerny-Turner spectrometer having a confocal distance of 300 nm and a diffraction grating of 300 gr/mm. For example, Acton SP-300i manufactured by Princeton Instruments may be used for the spectrometer 46.

According to the embodiment, the high-sensitivity camera 48 is configured as a high-sensitivity sCMOS microscope camera. For example, ORCA-Flash 4.0 V2 manufactured by Hamamatsu Photonics K.K. may be used for the high-sensitivity camera 48.

In the transcriptome estimation device 20 configured as described above, the laser beam of wavelength 532 nm emitted from the laser 22 is reflected by the mirror 24, is filtered to the laser beam of only the wavelength 532 nm by the bandpass filter 26 and is subjected to adjustment of the beam diameter by the beam expander 28. The laser beam of the adjusted beam diameter is reflected by the dichroic mirror 30, is guided to the 90/10 mirror 34 by the mirrors 32 and 33, is reflected by the 90/10 mirror 34 and is radiated to the measurement object (objective cells 10) by the object lens 40. The detected light such as the reflected light or the scattered light from the measurement object (objective cells 10) is reflected by the 90/10 mirror 34 and is guided to the dichroic mirror 30 by the mirrors 32 and 33. The Rayleigh scattered light out of the detected light is reflected by the dichroic mirror 30, while the Stokes light of wavelength equal to or higher than 532 nm is transmitted through the dichroic mirror 30. The detected light (Stokes light) transmitted through the dichroic mirror 30 enters the edge filter 36 that transmits only the Stokes light, while cutting the Rayleigh scattered light, which the dichroic mirror 30 fails to cut, and then enters the spectrometer 46 via the lens 38 and the confocal pinhole 44. The detected light (Stokes light) entering the spectrometer 46 is dispersed by the spectrometer 46 to expose corresponding pixels of the high-sensitivity camera 48 according to the intensity. The resulting Raman scattering spectra are analyzed by the PC 50 for estimation of transcriptomes in the objective cells 10.

Figure 2:
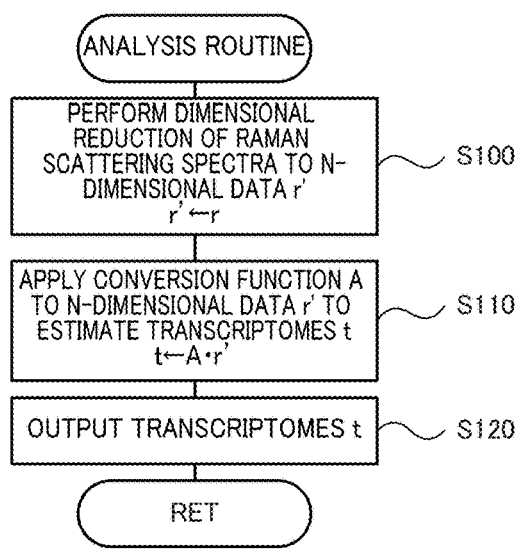
FIG. 2 is a flowchart showing one example of an analysis routine.

The PC 50 performs an analysis routine shown in FIG. 2 to analyze Raman scattering spectra and estimate transcriptomes in the objective cells 10. The analysis routine of FIG. 2 first performs dimensional reduction of Raman scattering spectra r to N-dimensional Raman data r' (step S100). The N-dimensional Raman data r' is obtained by dimensional reduction of Raman scattering spectra of cells in M different conditions to characteristic N-dimensional spectra. The analysis routine subsequently estimates transcriptomes t with regard to the N-dimensional Raman data r' using a function A determined by linear regression of a relationship between the N-dimensional Raman data r' and data of transcriptomes (step S110). The analysis routine then outputs the estimated transcriptomes t (step S120) and is terminated.

Figure 3:
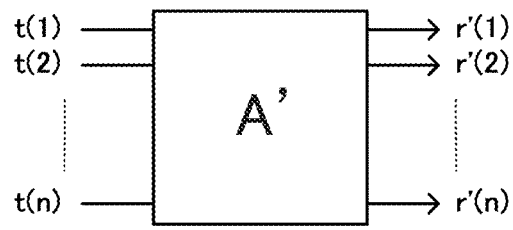
FIG. 3 is a diagram illustrating a function A'.

As shown in FIG. 3, a function A' is determined for linear regression of N-dimensional Raman data r'(1) to r'(n) obtained by N-dimensional reduction of Raman scattering spectra of a plurality of cells in M different conditions from transcriptomes t(1) to t(n) of the plurality of cells, and the function A is then determined as an inverse function of the function A'.

Figure 4:
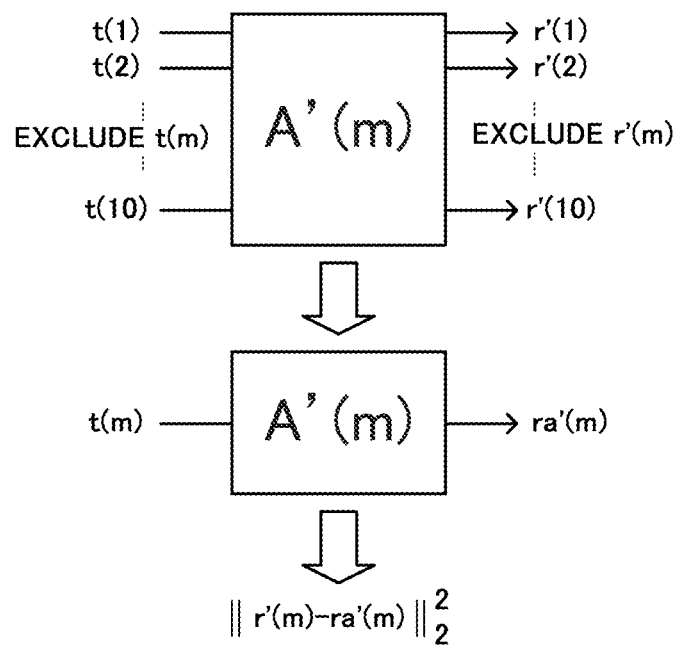
FIG. 4 is a diagram illustrating a method of determining a function A'(m) of an appropriate combination and a method of calculating a square error between nine-dimensional Raman data ra'(m) estimated by the function A'(m) and nine-dimensional Raman data r'(m)

The following describes that the function A determined as described above is adequate. The function A' is first discussed. There are provided transcriptomes t(1) to t(10) of a plurality of cells in ten different conditions and nine-dimensional Raman data r'(1) to r'(10) obtained by nine-dimensional reduction of Raman scattering data r of the plurality of cells. As shown in FIG. 4, a function A'(m) is determined by using transcriptomes t(1) to t(10) other than t(m) of a plurality of cells in any nine different conditions and their nine-dimensional Raman data r'(1) to r'(10) other than r'(m). Nine-dimensional Raman data ra'(m) is subsequently obtained by applying the function A'(m) to a transcriptome t(m) that is not used for estimation of the function A'(m). A square error of a difference between the obtained nine-dimensional Raman data ra'(m) and the corresponding nine-dimensional Raman data r'(m) is then calculated. A sum of ten square errors calculated with regard to all the values m (m is equal to 1 to 10) is calculated as a PRESS value of the function A' of the appropriate combination.

Figure 5:
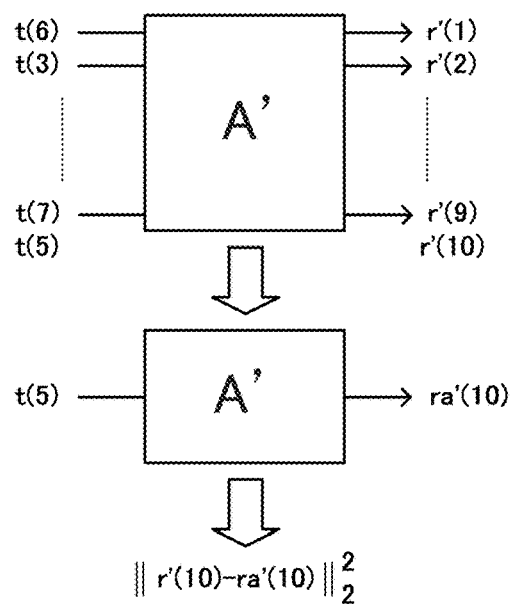
FIG. 5 is a diagram illustrating a method of determining a function A' of an inappropriate combination and a method of calculating a square error between nine-dimensional Raman data ra'(10) estimated by the function A' and nine-dimensional Raman data r'(10)

The following describes combinations of transcriptomes t(1) to t(10) of a plurality of cells in ten different conditions and nine-dimensional Raman data r'(1) to r'(10) of the plurality of cells in non-corresponding conditions. For example, as shown in FIG. 5, the nine-dimensional Raman data r'(1), r'(2), . . . , r'(9) and r'(10) are made to correspond to the transcriptomes t(6), t(3), . . . , t(7), and t(5). A function A' is determined by using all the corresponding combinations excluding one combination (the combination of t(5) and r'(10) in the illustrated example of FIG. 5), and nine-dimensional Raman data ra'(10) is obtained by applying the function A' to the transcriptome t(5) of one excluded combination. A square error of a difference between the obtained nine-dimensional Raman data ra'(10) and the corresponding nine-dimensional Raman data r'(10) is calculated. A sum of ten square errors calculated by changing one excluded combination is calculated as a PRESS value of the function A' of the inappropriate combination. PRESS values of the functions A' of inappropriate combinations are similarly calculated by changing the combinations of the transcriptomes t(1) to t(10) of the plurality of cells in the ten different conditions and the nine-dimensional Raman data r'(1) to r'(10) of the plurality of cells in the non-corresponding conditions. The PRESS value of the function A' of the inappropriate combination is a number of about the factorial of 10.

For verification, a plurality of cells were made alive in ten different conditions, and a PRESS value of the function A' of an appropriate combination and PRESS values of the functions A' of inappropriate 10000 combinations selected at random were calculated:

(1) Liquid culture with Yeast Extract (YE)+3% Glucose culture medium at 30° C. for 24 hours;
(2) Liquid culture with YE+3% Glucose+1 mmol/L Sorbitol culture medium at 30° C. for 1 hour;
(3) Liquid culture with YE+3% Glucose+1 mmol/L $CdSO_4$ culture medium at 30° C. for 1 hour;
(4) Liquid culture with YE+3% Glucose+2 mmol/L $H_2O_2$ culture medium at 30° C. for 1 hour;
(5) Liquid culture with YE+3% Glucose culture medium at 39° C. for 1 hour;
(6) Liquid culture with YE+3% Glucose+10% Ethanol culture medium at 30° C. for 24 hours;
(7) Liquid culture with Edinburgh Minimal Medium (EMM) culture medium at 30° C. for 24 hours;
(8) Liquid culture with EMM culture medium containing 0.1% Glucose at 30° C. for 24 hours;
(9) Liquid culture with EMM culture medium excluding Glucose at 30° C. for 24 hours; and
(10) Liquid culture with EMM culture medium excluding $NH_4Cl$ at 30° C. for 24 hours.

Figure 6:
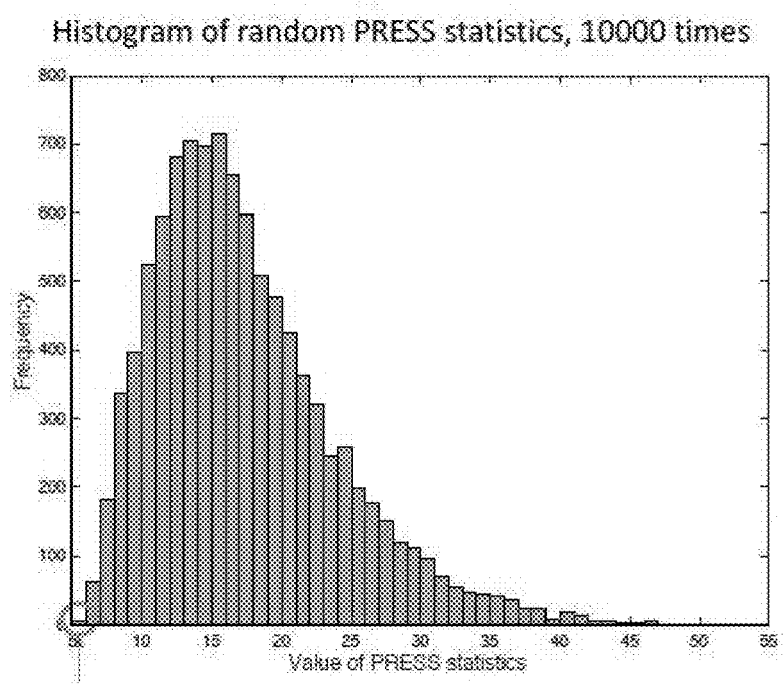
FIG. 6 is a graph showing a histogram of PRESS values with regard to a function A' of an appropriate combination and functions A' of inappropriate combinations.

FIG. 6 shows a histogram of the calculated PRESS value of the function A' of the appropriate combination and the calculated PRESS values of the functions A' of the 10000 inappropriate combinations. The PRESS value of the function A' of the appropriate combination was about 5.77 and was included in a minimum level of the histogram of FIG. 6. The probability of appearance of the smaller PRESS values than the PRESS value of the function A' of the appropriate combination was 0.02%. These results show that the data obtained by applying the function A' of the appropriate combination to the transcriptomes t(1) to t(9) of the plurality of cells in the nine different conditions well agree with the nine-dimensional Raman data r'(1) to r'(9) of the plurality of cells in the corresponding conditions with slight errors. This verification proves that the function A' of the appropriate combination is adequate.

Figure 7:
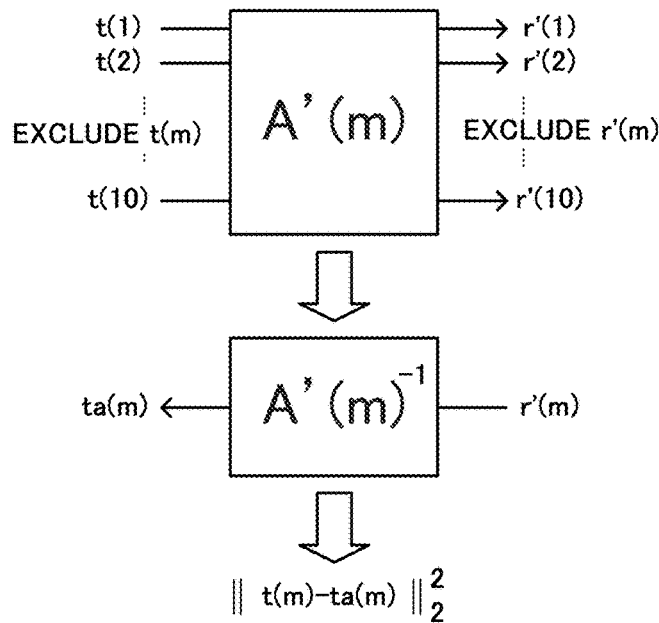
FIG. 7 is a diagram illustrating the method of determining the function A'(m) of the appropriate combination and a method of calculating a square error between a transcriptome ta(m) estimated by an inverse function of the function A'(m) of the appropriate combination and a transcriptome t(m)

The function A as the inverse function of the function A' is discussed next. With regard to the transcriptomes t(1) to t(10) of the plurality of cells in the ten different conditions and the corresponding nine-dimensional Raman data r'(1) to r'(10), a function $A'(m)^{-1}$ is determined as an inverse function of the function A'(m) determined by using the transcriptomes t(1) to t(10) other than t(m) of the plurality of cells in any nine different conditions and their nine-dimensional Raman data r'(1) to r'(10) other than r'(m) as shown in FIG. 7. A transcriptome ta(m) is subsequently calculated by applying the function $A'(m)^{-1}$ to the nine-dimensional Raman data r'(m) that is not used for estimation of the function A'(m), and a square error between the calculated transcriptome ta(m) and the corresponding transcriptome t(m) is calculated. A sum of ten square errors calculated with regard to all the values m (m is equal to 1 to 10) is calculated as a PRESS value of the function $A(=A'^{-1})$ of the appropriate combination.

Figure 8:
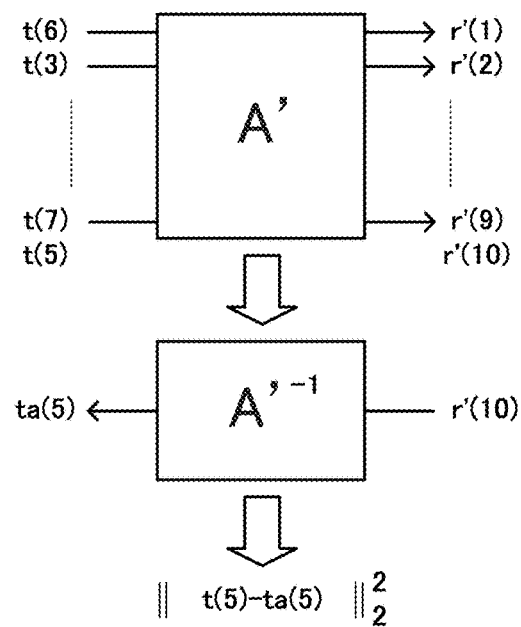
FIG. 8 is a diagram illustrating the method of determining the function A' of the inappropriate combination and a method of calculating a square error between nine-dimensional Raman data ra'(10) estimated by an inverse function of the function A' of the inappropriate combination and nine-dimensional Raman data r'(10)

With regard to the transcriptomes t(1) to t(10) of the plurality of cells in the ten different conditions and the corresponding nine-dimensional Raman data r'(1) to r'(10), as in the case of FIG. 5, the nine-dimensional Raman data r'(1), r'(2), . . . , r'(9) and r'(10) are made to correspond to the transcriptomes t(6), t(3), . . . , t(7), and t(5) as shown in FIG. 8. A function A' is determined by using all the corresponding combinations excluding one combination (the combination of t(5) and r'(10) in the illustrated example of FIG. 8), and a function $A'^{-1}$ as its inverse function is determined. A transcriptome ta(5) is subsequently calculated by applying the function $A'^{-1}$ to the nine-dimensional Raman data r'(10) of one excluded combination, and a square error between the calculated transcriptome ta(5) and the corresponding transcriptome t(5) is calculated. A sum of ten square errors calculated by changing one excluded combination is calculated as a PRESS value of the function $A(=A'^{-1})$ of the inappropriate combination. PRESS values of the functions $A(=A'^{-1})$ of inappropriate combinations are similarly calculated by changing the combinations of the transcriptomes t(1) to t(10) of the plurality of cells in the ten different conditions and the nine-dimensional Raman data r'(1) to r'(10) of the plurality of cells in the non-corresponding conditions. The PRESS value of the function $A(=A'^{-1})$ of the inappropriate combination is a number of about the factorial of 10.

Figure 9:
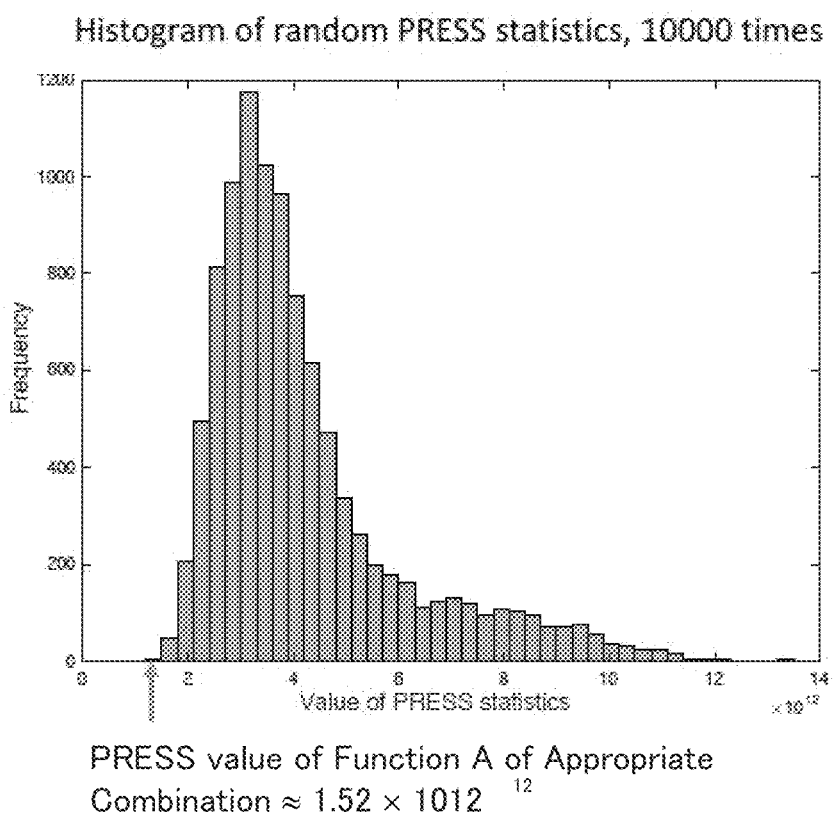
FIG. 9 is a graph showing a histogram of PRESS values with regard to an inverse function of the function A' of the appropriate combination and inverse functions of the functions A' of the inappropriate combinations.

A plurality of cells were made alive in the ten different conditions (1) to (10) used for the verification described above, and a PRESS value of the function $A(=A'^{-1})$ of an appropriate combination and PRESS values of the functions $A(=A'^{-1})$ of inappropriate 10000 combinations selected at random were calculated. FIG. 9 shows a histogram of the calculated PRESS value of the function $A(=A'^{-1})$ of the appropriate combination and the calculated PRESS values of the functions $A(=A'^{-1})$ of the 10000 inappropriate combinations. The PRESS value of the function $A(=A'^{-1})$ of the appropriate combination was about $1.52 \times 10^{12}$ and was included in a minimum level of the histogram of FIG. 9. The probability of appearance of the smaller PRESS values than the PRESS value of the function $A(=A'^{-1})$ of the appropriate combination was 0.03%. These results show that the data obtained by applying the function $A(=A'^{-1})$ of the appropriate combination to the nine-dimensional Raman data r'(1) to r'(9) of the plurality of cells in the nine different conditions well agree with the transcriptomes t(1) to t(9) of the plurality of cells in the corresponding conditions with slight errors. This verification proves that the function $A(=A'^{-1})$ of the appropriate combination is adequate.

The transcriptome estimation device 20 of the embodiment described above irradiates the objective cells 10 with the laser beam of wavelength 532 nm, obtains the Raman scattering spectra by dispersion of the resulting Stokes light, and applies the function A to the N-dimensional Raman data r' obtained by dimensional reduction of the Raman scattering spectra, so as to estimate the transcriptomes t of the objective cells 10. This configuration enables the transcriptomes t of the objective cells 10 to be estimated without destruction of the objective cells 10.

The transcriptome estimation method by the transcriptome estimation device 20 of the embodiment obtains the N-dimensional Raman data r' by dimensional reduction of the Raman scattering spectra of the cells in the M different conditions, calculates the function A on the assumption of the linear regression relationship between the transcriptomes t of the cells in the M different conditions and the corresponding N-dimensional Raman data r', and applies the function A to the N-dimensional Raman data r' obtained by dimensional reduction of the Raman scattering spectra r of the objective cells 10, so as to estimate the transcriptomes t of the objective cells 10. The verification described above proves that the function A is significantly adequate. This configuration thus enables the transcriptomes t of the objective cells 10 to be estimated adequately.

The transcriptome estimation device 20 of the embodiment uses the transcriptomes t(1) to t(10) of the plurality of cells in the ten different conditions and the corresponding nine-dimensional Raman data r'(1) to r'(10) for the verification of the function A. The number of the different conditions is, however, not limited to ten but may be any number, and the number of dimensions is not limited to nine but may be any number.

The transcriptome estimation device 20 of the embodiment determines the function A as the inverse function of the function A', which is determined by linear regression of the N-dimensional Raman data r' of the cells in the M different conditions from the transcriptomes t of the cells in the M different conditions. According to a modification, the function A may be determined by linear regression of the transcriptomes t of the cells in the M different conditions from the N-dimensional Raman data r' of the cells in the M different conditions.

The transcriptome estimation device 20 of the embodiment irradiates the objective cells 10 with the laser beam of wavelength 532 nm. This wavelength is, however, not essential, and laser beam of any wavelength may be used to provide Raman scattering.

The aspect of the disclosure is described above with reference to the embodiment. The disclosure is, however, not limited to the above embodiment but various modifications and variations may be made to the embodiment without departing from the scope of the disclosure.

INDUSTRIAL APPLICABILITY

The technique of the disclosure is preferably applicable to the manufacturing industries of the transcriptome estimation device and so on.

What is claimed is:

1. A transcriptome estimation device configured to estimate a transcriptome of an objective cell, the transcriptome estimation device comprising:
    a laser irradiator configured to irradiate the objective cell with laser beam of a predetermined wavelength;
    a light selector configured to select only Stokes light out of detected light including reflected light and scattered light by radiation of the laser beam;
    a spectroscope configured to disperse the selected Stokes light and output a Raman scattering spectrum; and
    an estimator configured to estimate the transcriptome of the objective cell, based on the Raman scattering spectrum.

2. The transcriptome estimation device according to claim 1,
    wherein the estimator performs dimensional reduction of the Raman scattering spectrum to N-dimensional Raman data, and estimates the transcriptome of the objective cell, based on the N-dimensional Raman data.

3. The transcriptome estimation device according to claim 2,
    wherein the estimator applies a conversion function that is based on a linear regression relationship between the N-dimensional Raman data of cells in M different conditions and transcriptomes of the cells in the M different conditions, to estimate the transcriptome.

4. The transcriptome estimation device according to claim 3,
    wherein the conversion function is determined as an inverse function of a function, which is determined by linear regression of the N-dimensional Raman data of the cells in the M different conditions from the transcriptomes of the cells in the M different conditions.

5. A transcriptome estimation method that estimates a transcriptome of an objective cell from a Raman scattering spectrum that is obtained by irradiation of the objective cell with laser beam of a predetermined wavelength, the transcriptome estimation method comprising:

obtaining N-dimensional Raman data by dimensional reduction of Raman scattering spectra of cells in M different conditions, and estimating a conversion function on assumption of a linear regression relationship between transcriptomes of the cells in the M different conditions and N-dimensional Raman data of the cells in the M different conditions; and estimating the transcriptome by applying the conversion function to N-dimensional Raman data obtained by dimensional reduction of a Raman scattering spectrum of the objective cell.

* * * * *